United States Patent
Cohen et al.

(10) Patent No.: US 7,635,070 B2
(45) Date of Patent: Dec. 22, 2009

(54) DROPPER BOTTLE AND ACCESSORIES THEREFOR

(75) Inventors: Ben Z. Cohen, 140 E. 80th St., New York, NY (US) 10021; Nigel Kelly, Rye Brook, NY (US)

(73) Assignee: Ben Z. Cohen, New York, NY (US)

( * ) Notice: Subject to any disclaimer, the term of this patent is extended or adjusted under 35 U.S.C. 154(b) by 754 days.

(21) Appl. No.: 10/523,516

(22) PCT Filed: Aug. 6, 2003

(86) PCT No.: PCT/US03/24484

§ 371 (c)(1),
(2), (4) Date: Oct. 19, 2005

(87) PCT Pub. No.: WO2004/013009

PCT Pub. Date: Feb. 12, 2004

(65) Prior Publication Data

US 2006/0108378 A1    May 25, 2006

Related U.S. Application Data

(60) Provisional application No. 60/401,397, filed on Aug. 6, 2002.

(51) Int. Cl.
*B67D 5/64* (2006.01)
(52) U.S. Cl. .............. 222/162; 222/183; 222/214; 222/215; 222/420; 604/295; 604/298
(58) Field of Classification Search ......... 222/211–215, 222/183, 162, 160, 164, 420, 182; 604/295, 604/298
See application file for complete search history.

(56) References Cited

U.S. PATENT DOCUMENTS

| 3,405,843 | A | * | 10/1968 | Watson, Jr. ................ 222/95 |
| 4,765,515 | A | * | 8/1988 | Lippman .................. 222/162 |
| 4,771,769 | A | | 9/1988 | Hegemann et al. |
| 4,860,738 | A | * | 8/1989 | Hegemann et al. ..... 128/200.22 |
| 5,133,702 | A | | 7/1992 | Py |
| 5,487,489 | A | * | 1/1996 | Weiss et al. ................ 222/1 |
| 5,673,822 | A | | 10/1997 | Chalmin et al. |
| 6,033,384 | A | | 3/2000 | Py |
| 6,305,580 | B1 | * | 10/2001 | Chen ....................... 222/162 |

\* cited by examiner

*Primary Examiner*—Frederick C. Nicolas
(74) *Attorney, Agent, or Firm*—Hoffmann & Baron, LLP

(57) ABSTRACT

To overcome shortcomings of the prior art, the subject invention is provided which includes various dropper bottle designs and dropper bottle assemblies including accessories for dropper bottles. With certain aspects of the subject invention, improvements in the administration of eye drops is provided by adding accessories or modifications to conventional dropper bottles, so that doses and/or single drops may be administered in a repeatable and reliable manner. More specifically, certain embodiments use devices (10, 300) to restrict the amount the dropper bottle (12) is deformed in administering a dose; other embodiments rely on mechanical reduction of interior volume (without deformation of the dropper bottle (12)) to administer a dose, such as with a displaceable piston (500, 602); and, yet, a further embodiment provides a valving arrangement (402, 404) to limit a dose. Features (200) are also included which aid in the alignment of the dropper bottle's nozzle to the eye, and a feature (102) is provided for protecting the user's eye from potential damage which can occur if a pointed nozzle (104) is brought into contact with the eye during alignment. As will be appreciated by those skilled in the art, the various aspects and embodiments disclosed herein may be used singularly or in various combinations.

8 Claims, 16 Drawing Sheets

DROPPER BOTTLE AND ACCESSORIES THEREFOR

This application claims priority to U.S. Provisional Patent Application No. 60/401,397, filed Aug. 6, 2002.

Conventional dropper bottles for administering ophthalmic fluid are well known in the prior art. The basic commercial design of such dropper bottles has remained fairly unchanged over the last several decades: a squeezable container is provided with a tapered dispenser that terminates in a discharge aperture. To administer ophthalmic fluid, the discharge aperture is aligned above a target eye and the bottle is squeezed to urge out a drop or dose of the fluid.

Although the conventional design is widely used, it suffers from several drawbacks. Primarily, dose volume is difficult to repeatedly control, in part, because a proper amount of squeeze force is difficult to repeatedly apply to the dropper bottle. Also, accurate control over and targeting of dose placement are difficult to obtain.

SUMMARY OF THE INVENTION

To overcome shortcomings of the prior art, the subject invention is provided which includes various dropper bottle designs and dropper bottle assemblies including accessories for dropper bottles. With certain aspects of the subject invention, improvements in the administration of eye drops is provided by adding accessories or modifications to conventional dropper bottles, so that doses and/or single drops may be administered in a repeatable and reliable manner. More specifically, certain embodiments restrict the amount the dropper bottle is deformed in administering a dose; other embodiments rely on mechanical reduction of interior volume (without deformation of the dropper bottle) to administer a dose, such as with a displaceable piston; and, yet, a further embodiment provides a valving arrangement to limit a dose. Further features are included which aid in the alignment of the dropper bottle's nozzle to the eye, and also protect the user's eye from potential damage which can occur if a pointed nozzle is brought into contact with the eye during alignment. As will be appreciated by those skilled in the art, the various aspects and embodiments disclosed herein may be used singularly or in various combinations.

Unless indicated otherwise, any conventional dropper bottle design and component may be utilized with the subject invention. It should also be understood that reference to a "nozzle" does not require that a converging discharge passage be provided. Any shaped discharge passage can be utilized with the subject invention consistent with the following description. The subject invention is particularly well-suited for ophthalmic applications (i.e., dispensing of eye-related fluids).

These and other features of the subject invention will be better understood through a study of the following detailed description and accompanying drawings.

DETAILED DESCRIPTION OF THE INVENTION

Several embodiments of the subject invention are directed to the problem that most current dropper bottles require the bottle to be deformed, e.g. squeezed, in order to generate pressure inside the bottle and, thereby, expel a dose or drop. This practice is problematic because the user is often unable to determine how hard to press the bottle, and for how long a period of time, so that a single drop is expelled. Usually, more than one drop is expelled, which may be wasteful and messy.

Figure 1:
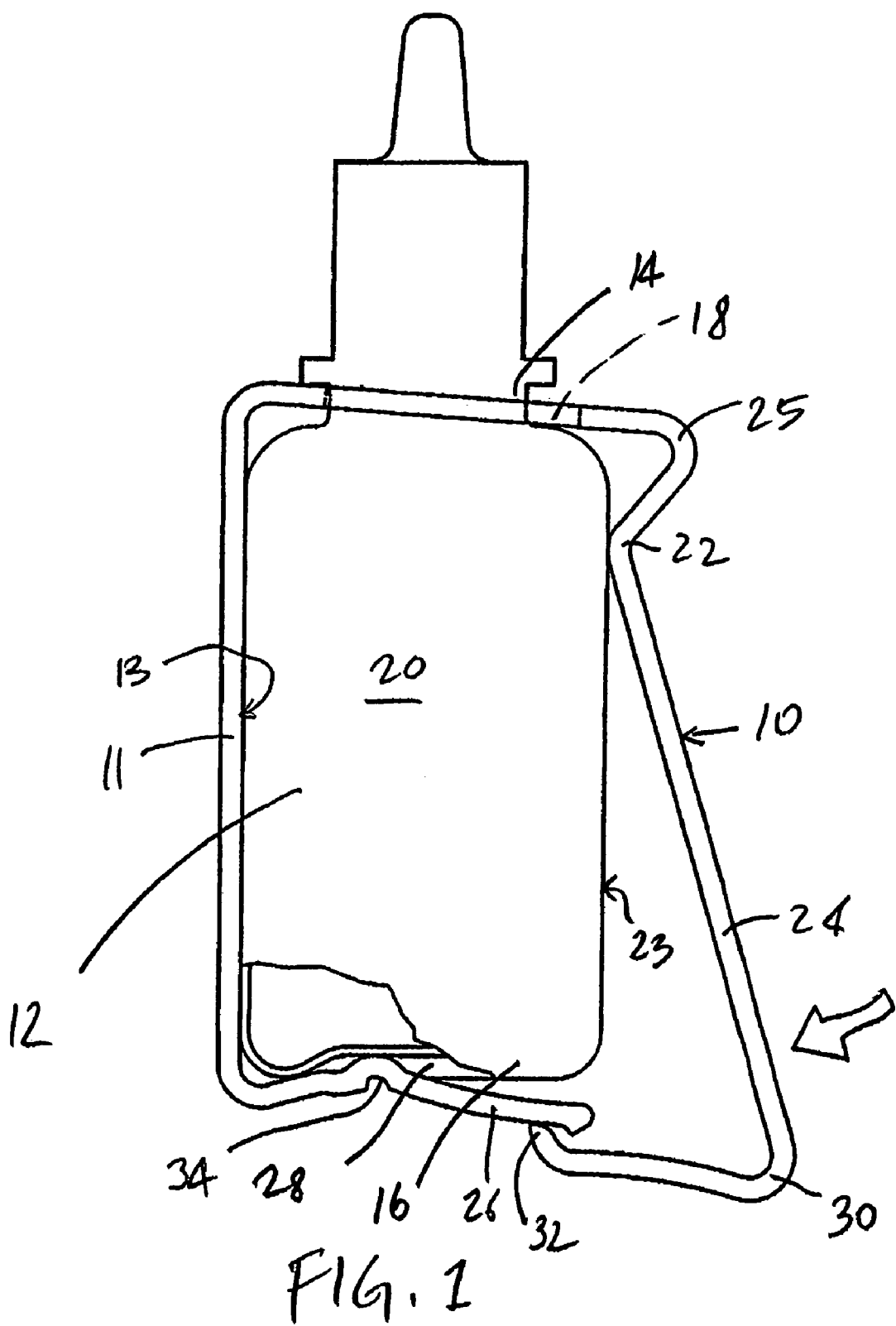
FIGS. 1-3 show a dropper bottle assembly including a cradle for controllably deforming the dropper bottle in causing dose administration therefrom.
Figure 2:
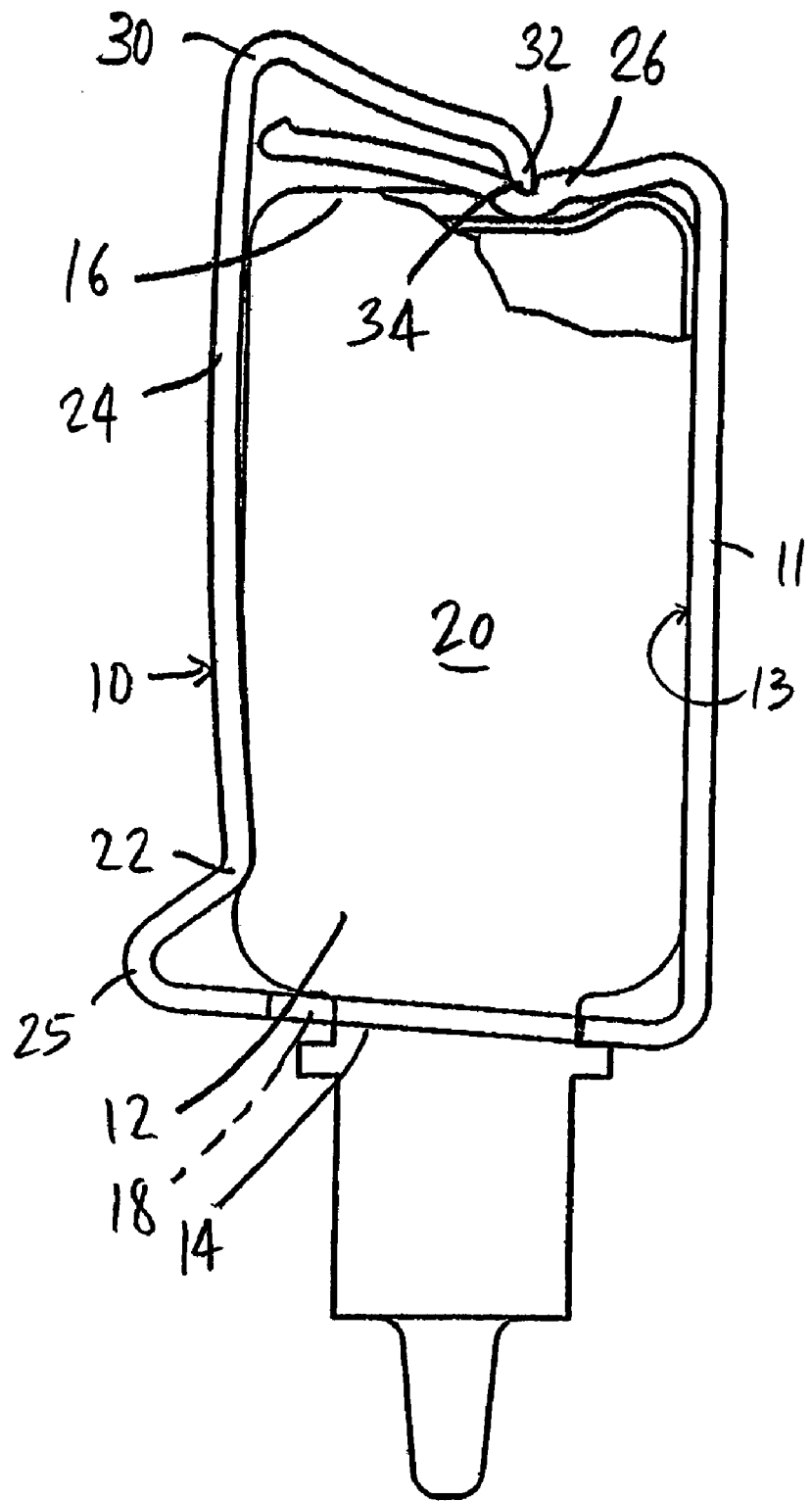
Figure 3:
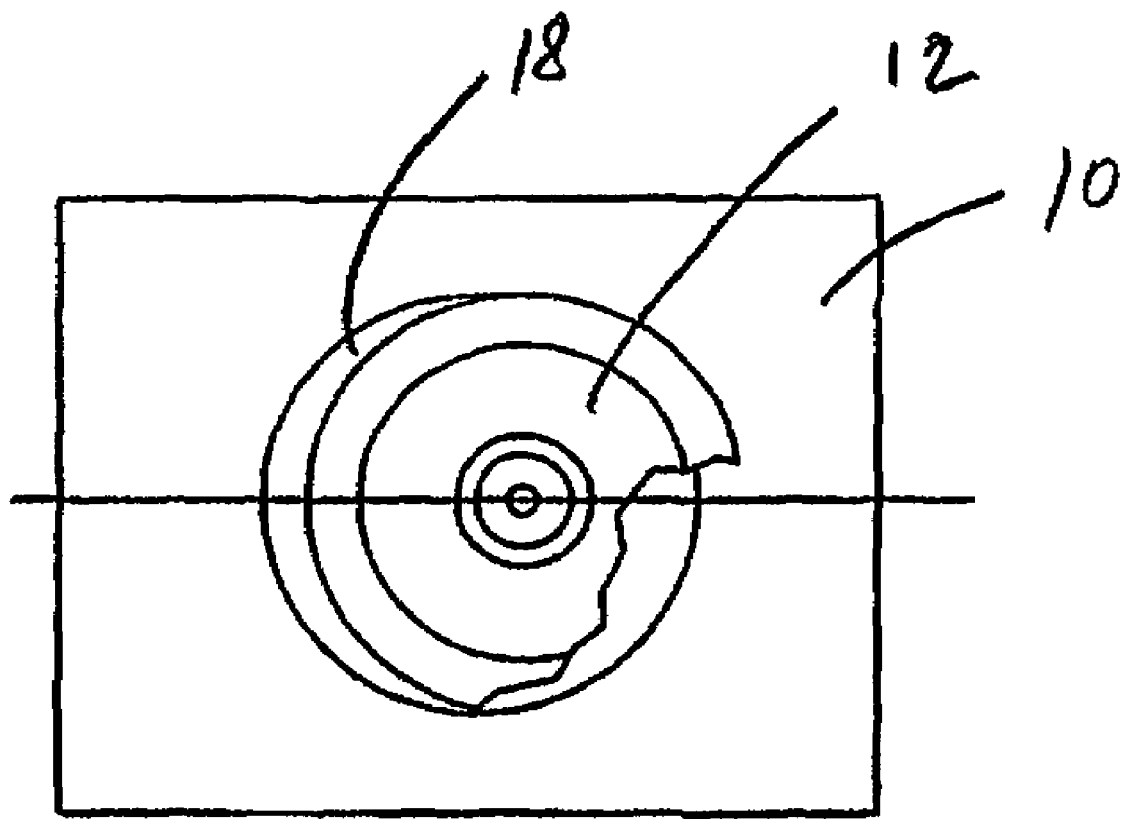

With reference to FIGS. 1-3, and in a first aspect of the subject invention, a cradle 10 is depicted which is formed to mount onto a dropper bottle 12 preferably by resiliently snapping onto the bottle 12 at the neck 14 and base 16. Preferably, the cradle 10 is formed of a resilient material, more preferably, a resilient thermoplastic. Mounting of the cradle 10 onto the neck 14 is facilitated by the provision of a hole 18 formed large enough to allow the bottle 12 to partially pass therethrough. In particular, the neck 14 of the bottle 12 may pass through the hole 18; preferably, however, the hole 18 is sized to not allow the passage therethrough of the reservoir 20 of the bottle 12. Once the cradle 10 is mounted, the bottle neck 14 is preferably pushed off-center from the hole 18 (FIG. 3) due to pressure exerted transversely by a portion 22 of cradle lever 24 against an outer wall 23 that defines the reservoir 20. The bottle 12 is further confined by side plate 11 of the cradle 10. The portion 22 presses the bottle 12 against inner surface 13 of the side plate 11. Preferably, the portion 22 is bent. In addition, the lower end 26 of the cradle 10 may seat in an indentation 28 in the base 16 of the bottle 12 and resiliently press thereagainst. As such, the cradle 10 preferably traps the bottle 12 at multiple points: at the hole 18; at the portion 22; at the inner surface 13; and at the lower end 26 of the cradle 10. As will be appreciated by those skilled in the art, the cradle 10 may be configured otherwise to mount onto the dropper bottle 12. The cradle 10 may be formed to be removable so as to be re-used with other dropper bottles or formed to be non-removably mounted to the dropper bottle, thus requiring to be discarded with a spent dropper bottle.

In use, free end 30 of the cradle lever 24 is pressed towards the bottle 12 as the bottle 12 is inverted to deliver one or more drops. As the free end 30 is pressed inwardly, and as shown in FIG. 2, the portion 22 indents a side of the reservoir 20 adjacent to the neck 14, thus deforming the outer wall 23 and reducing the volume of the reservoir 20. As a result, one or more drops may be controllably expelled. The dosage amount may be fixed to a predetermined extent of movement of the cradle lever 24, such as by example, restricting movement of the cradle lever 24 with a stop member. Optionally, at the point where the predetermined drop(s) are expelled (i.e., at a predetermined extent of movement of the cradle lever 24), the user may be alerted to a complete dosing wherein a toe 32 of the cradle lever 24 may nest into a recess 34 defined in the lower end 26, with an audible and/or tactile 'click' indicating that the desired drop(s) have been released from the bottle 12. Upon detecting this 'click', the user may release the free end 30 of the lever 24, which returns back to its fully open rest position (shown in FIG. 1). Preferably, hinge 25 provides a biasing force to urge the lever 24 to the rest position as shown in FIG. 1, where the dropper bottle 12 is undeformed or substantially undeformed. Further drops may then be released. Preferably, the hinge 25 also exerts a biasing force to press the portion 22 against the outer wall 23 without causing deformation or substantial deformation of the reservoir 20 so that unwanted dosing is avoided. To achieve this structure, the cradle 10 can be formed with the portion 22 in its natural state so as to overlap the reservoir 20. Likewise, the lower end 26 of the cradle 10 may be formed to overlap the reservoir 20.

Figure 4:
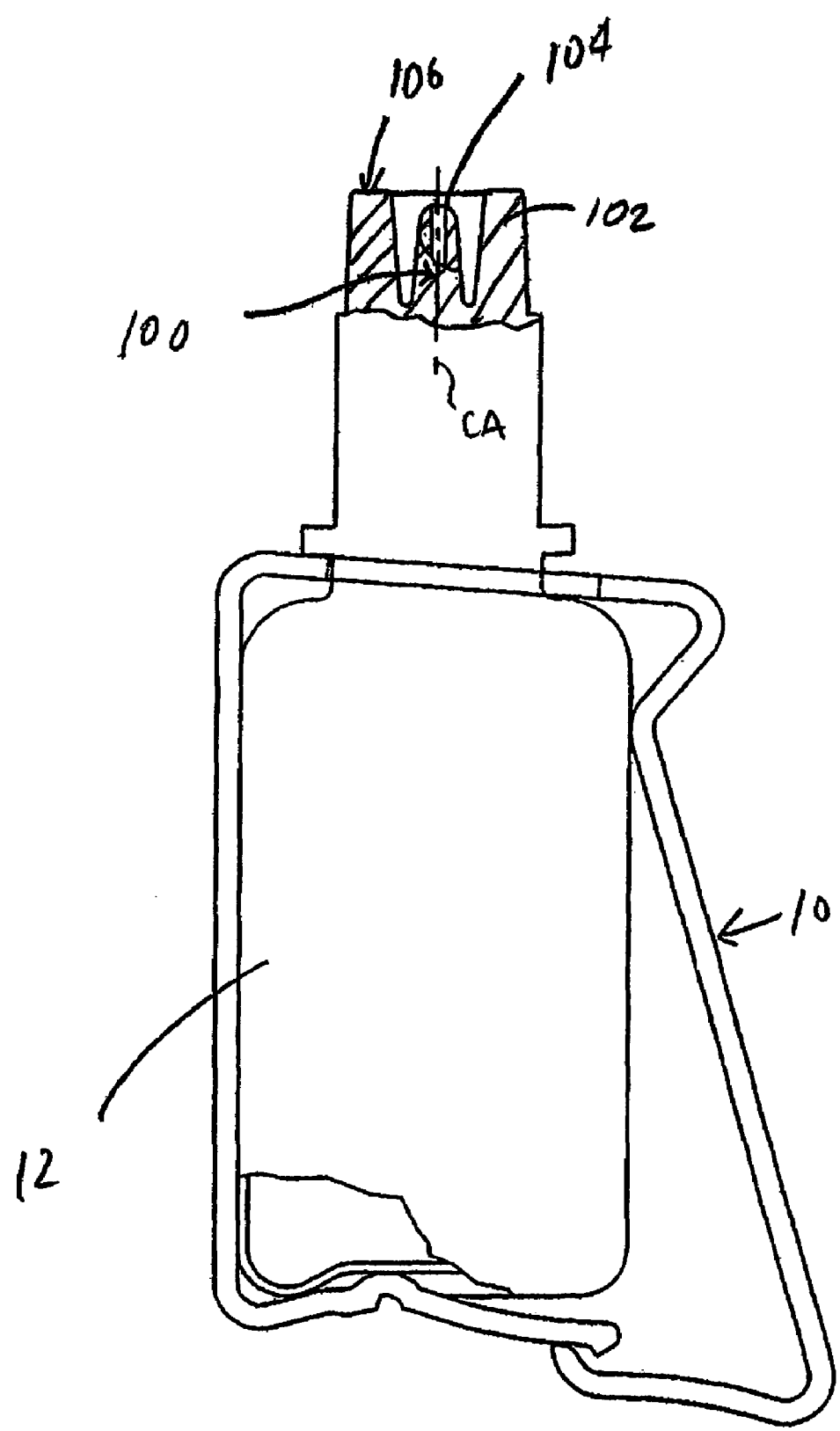
FIG. 4 is a dropper bottle similar to that of FIGS. 1-3 but with a collar disposed about its nozzle.

As shown in FIG. 4, and in a second aspect of the subject invention, a nozzle 100 may be provided on the dropper bottle 12 which is at least partially surrounded by a protruding outer collar 102. Preferably, the collar 102 terminates in a generally flat free end 106, and, more preferably, the free end 106 is disposed generally normally to central axis CA of the nozzle 100. Also, the collar 102 is preferably annular. The collar 102 encompasses a volume in which tip 104 of the nozzle is located. As a result, the collar 102 projects beyond the tip 104 of the nozzle 100 such that, if contact is made with an eye during use, the outer collar 102 will contact the eye and not the nozzle tip 104. The free end 106 at the front of the collar 102 will be less likely to cause the user any eye damage than the sharper nozzle tip 104. The nozzle 100 may be constructed from plastics such as polyethylene or polypropylene, or softer elastomers may be used as a further safety measure.

In a third aspect of the subject invention, a nozzle of a dropper bottle (e.g. nozzle 100) may be colored to further aid in the alignment process. As such, the nozzle 100 is non-transparent and non-translucent and provided with a non-white color. Colors are more easily visible to the eye than the colorless plastics used in conventional dropper bottle nozzles and a colored nozzle will be easier to visually align. The nozzle 100 may also be of a different color from its associated reservoir to provide additional contrast and improved visibility of the nozzle 100. Further, colors may be used for the nozzle 100 or around the nozzle 100 to denote the contents of the dropper bottle.

Figure 5:
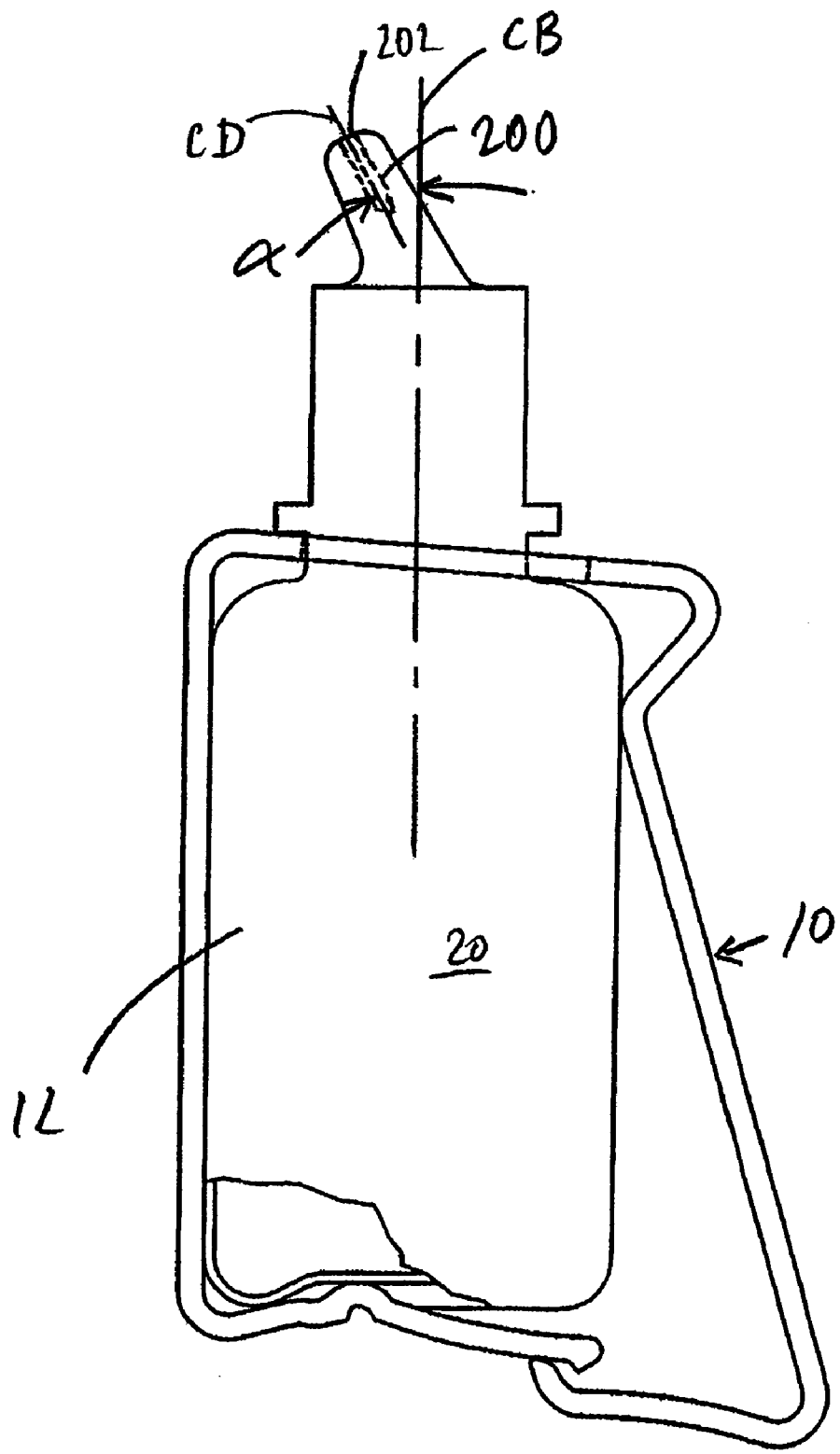
FIG. 5 is a dropper bottle similar to that of FIGS. 1-3 but with an angled nozzle.

As a further aid to alignment, as shown in FIG. 5, nozzle 200 may be directed at an angle to aid the placement of drops into the eye. Here, discharge aperture 202 is spaced from a central axis CB of reservoir 20. Preferably, the nozzle 200 is formed symmetrically along at least a portion of a central axis CD which is angularly disposed to the central axis CB. Angle α is defined between the central axes CD and CB and may be in the range of greater than 0° to approximately 135°.

Figure 6:
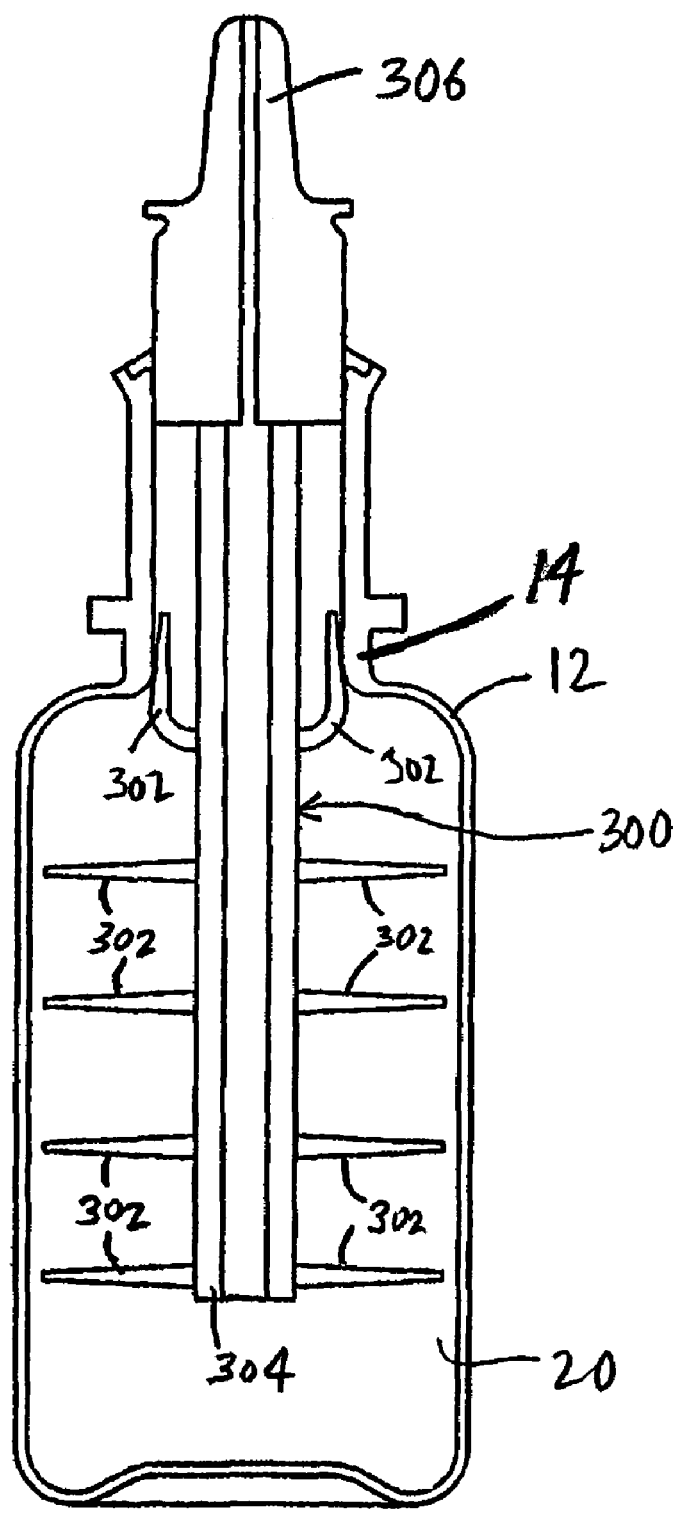
FIGS. 6-8 show the assembly and operation of a webbed structure in a dropper bottle for limiting deformation of the dropper bottle.
Figure 7:
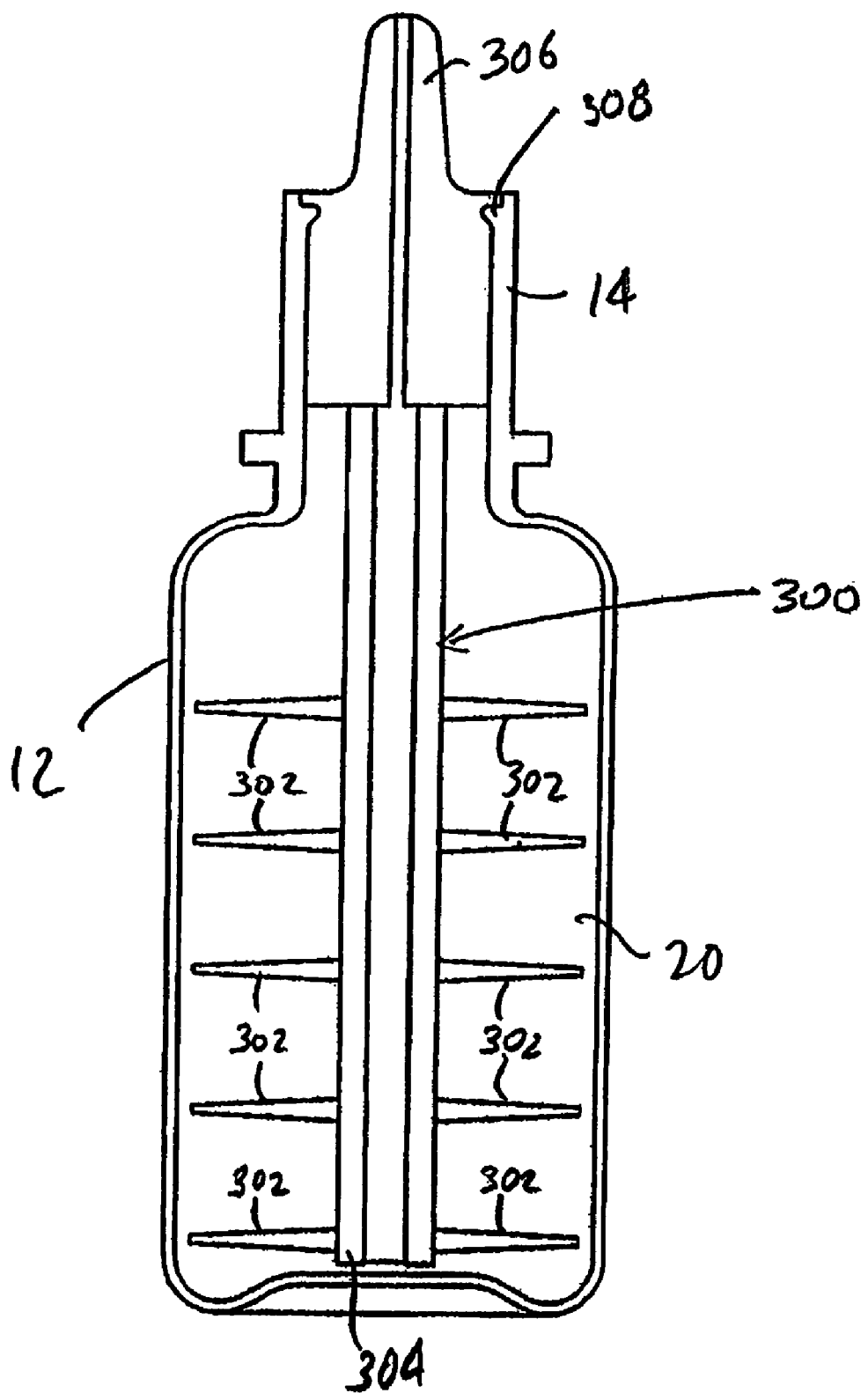
Figure 8:
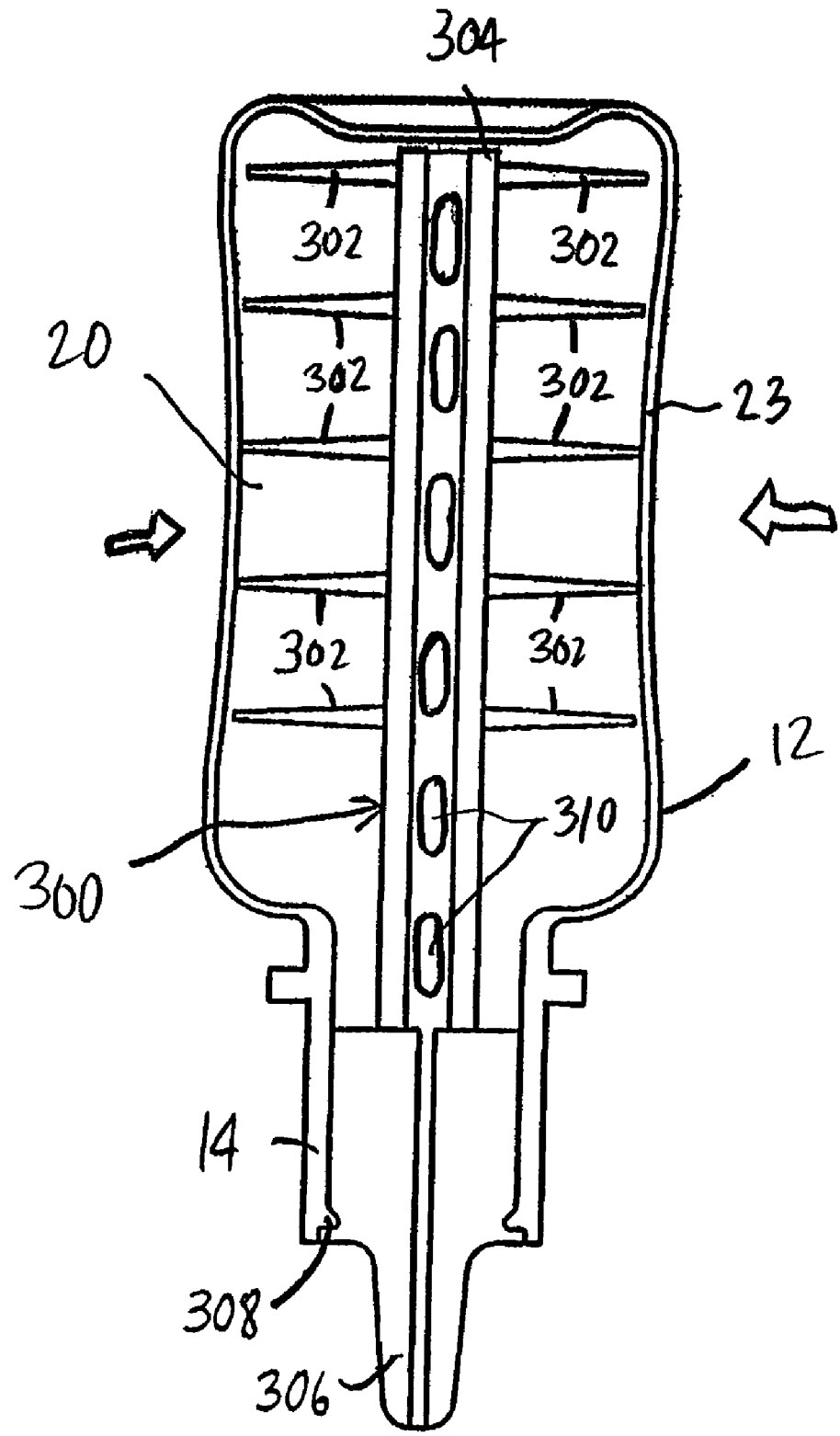

In a fourth aspect of the subject invention, and with reference to FIGS. 6-8, a device 300 is provided which limits the degree of deformation of the dropper bottle 12 to such an amount necessary to expel one dose or drop. The device 300 includes at least one, preferably a series of, outwardly-extending webs 302, like tree branches, which project from a central column 304 that is in communication with nozzle 306 and the reservoir 20. Preferably, the central column 304 is fixed to the nozzle 306, such as by being formed integrally therewith, in forming the device 300. Any method may be used to fix the device 300 to the bottle 12 including an interference fit in the neck 14 of the bottle 12. A locking detent 308 may also be provided to enhance the fixation of the device 300 to the bottle 12.

The column 304 may optionally be formed with one or more apertures 310, as shown in FIG. 8, to communicate the interior of the column 304 with the reservoir 20.

By way of non-limiting example, for installation, the device 300 may be inserted through the neck 14 with the webs 302 bending backwards through the neck 14 (FIG. 6) and returning to their original shape (FIG. 7) whilst in the reservoir 20 after installation. As shown in FIG. 8, once installed, the webs 302 are shaped and configured to limit the amount of deformation of the outer wall 23 to a predetermined amount in limiting the amount to be dosed (FIG. 8).

Although the webs 302 may be formed sufficiently resilient to pass through the neck 14, the webs 302 need sufficient strength in compression to resist buckling and excessive deformation of the outer wall 23. It is preferred that the webs 302 be disposed generally normally to the generally cylindrical portion of the outer wall 23. Also, as will be appreciated by those skilled in the art, the webs 302 can be formed as annular discs as shown in the Figures or in other various configurations and supported in any manner.

Figure 9:
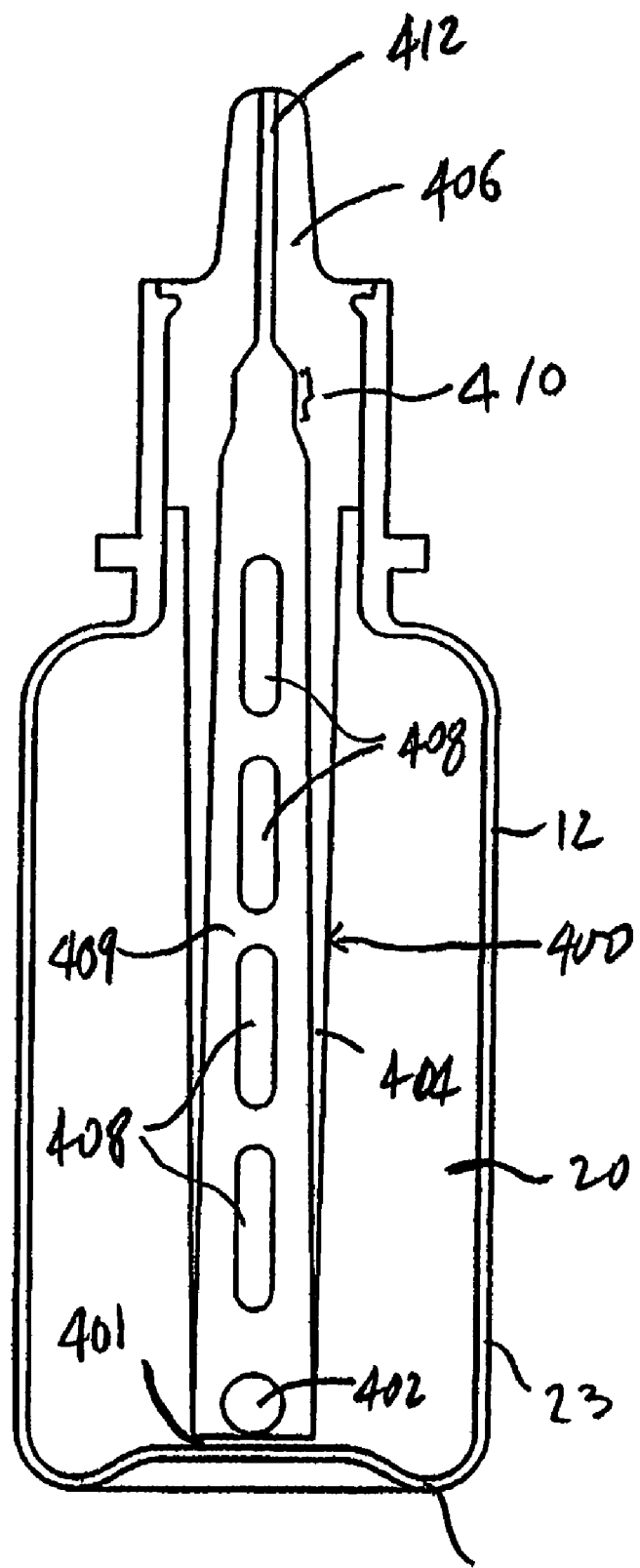
FIGS. 9-11 show a dropper bottle having a tube therein with a check valve ball; and, FIGS. 12-16 show different piston configurations for reducing the interior volume of a dropper bottle in causing dose administration therefrom.
Figure 10:
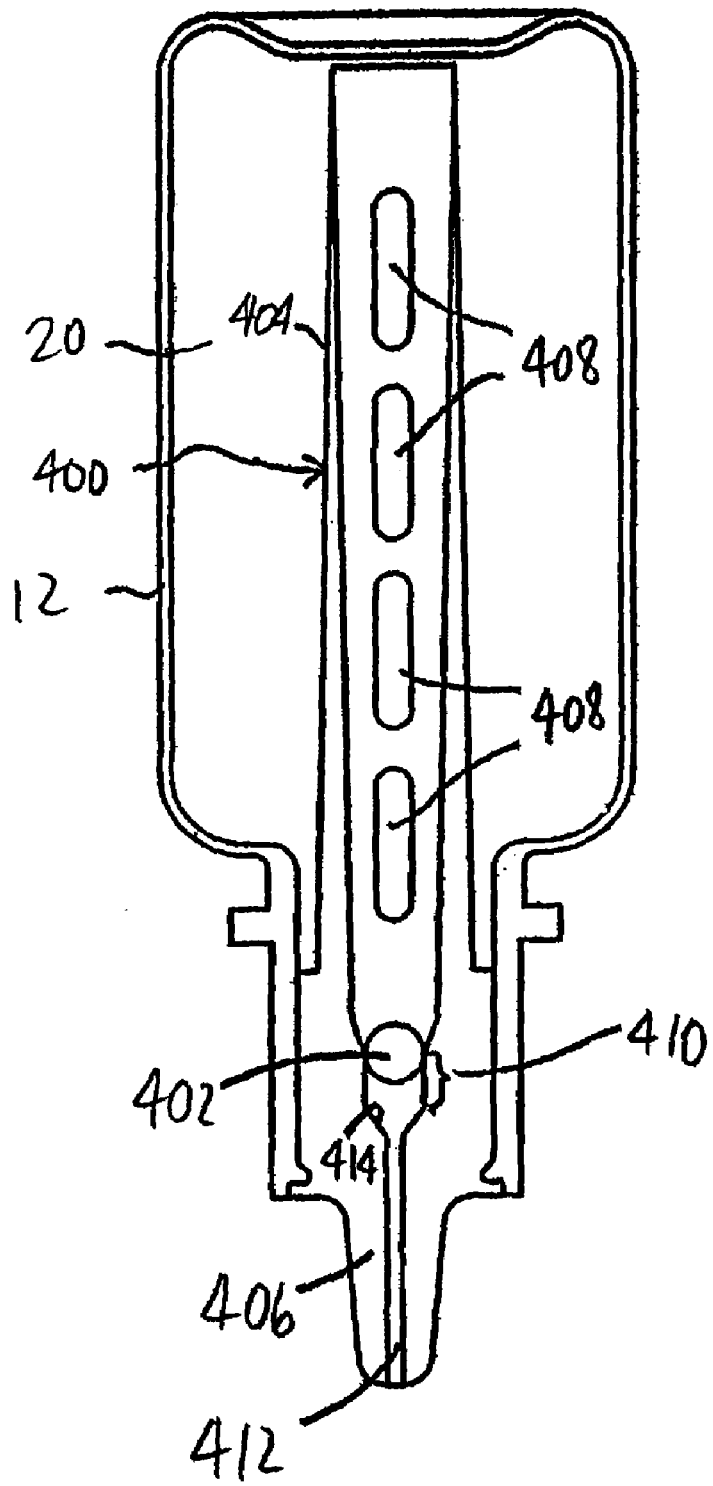
Figure 11:
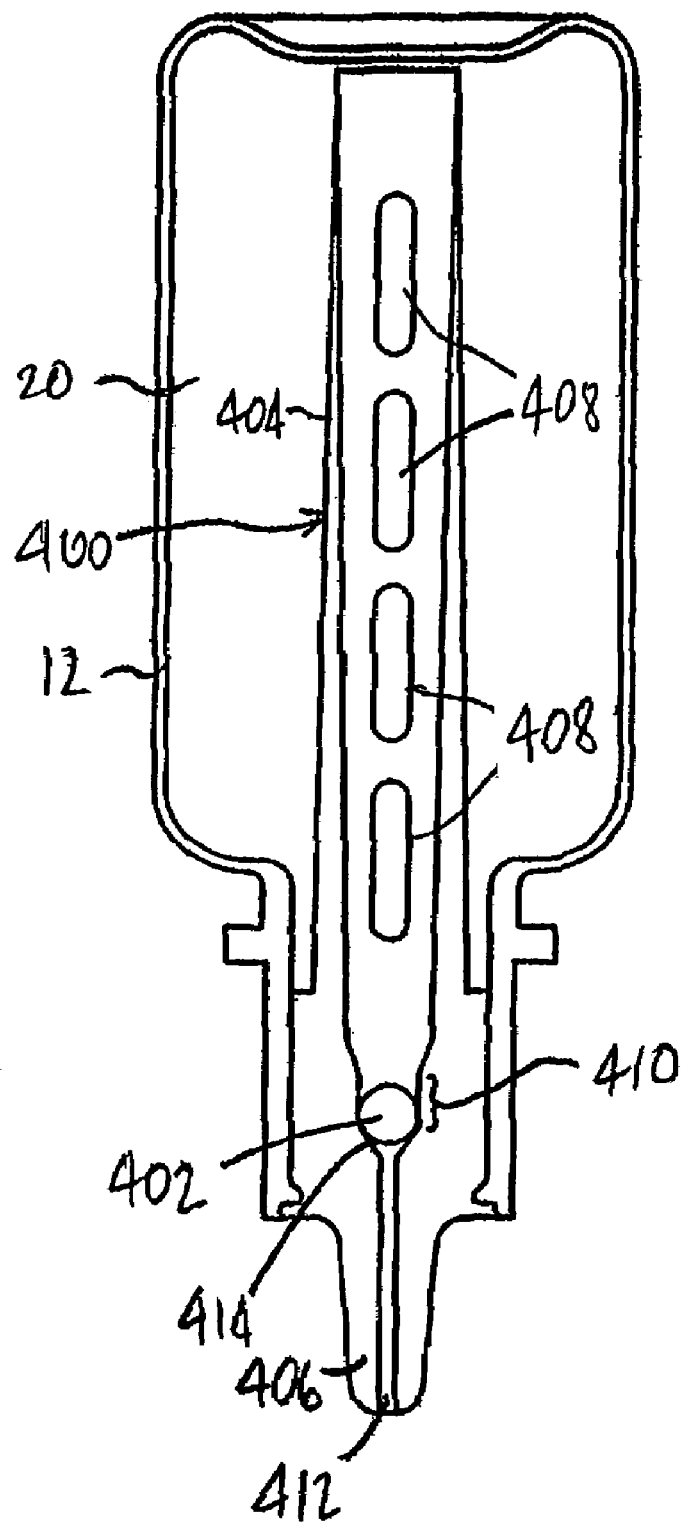

In a fifth aspect of the subject invention, and as shown in FIGS. 9-11, a device 400 is provided which limits the amount of liquid dispensed by a dropper bottle 12 to one drop or dose. The device 400 generally includes a check valve ball 402 which is free to run within a tube 404. The tube 404 extends from nozzle 406 and has a number of slots or openings 408 formed therethrough which allow fluid communication between inside 409 of the tube 406 and the reservoir 20. Also, the end of the tube 406 may be spaced from the outer wall 23, such as at the base 16, with the tube 404 communicating with the reservoir 20 via spacing 401. Preferably, the tube 404 is formed to continuously maintain the ball 402 therewithin. As such, the openings 408 and the spacing 401 may be sized to not permit passage therethrough of the ball 402. The end of the tube 404 adjacent to the nozzle 406 has a first section 410 sized to receive the ball 402 therewithin so as to form a fluid seal therewith. Portions of the tube 404 adjacent the first section 410 are generally larger than the first section 410. The first section 410 communicates with discharge passage 412 of the nozzle 406 and preferably encompasses a volume at least equal to a single dose to be administered by the dropper bottle 12.

In use, the ball 402 drops to the bottom of the bottle 12 when the bottle is upright and rested on its base 16 (FIG. 9). As the bottle 12 is inverted for use (with the nozzle 406 being directed downwards) (FIGS. 10-11), liquid in the reservoir 20 enters the openings 408 to flood the inside of the tube 404, and the ball 402 drops down through the tube 404 towards the nozzle 406. As the ball 402 reaches the first section 410, the first section 410 is already flooded and fully charged with liquid (FIG. 10). The ball 402 generally seals the first section 410 from remaining portions of the tube 404. By applying pressure to the wall of the reservoir 20 (such as with normal drop administration), fluid within the reservoir 20 is pressurized which forces the ball 402 through a defined stroke of the first section 410. In turn, the ball 402 displaces fluid along its path through the first section 410 resulting in an expelled drop of equal volume to the swept volume of the ball 402 (swept volume being the displaced volume during travel of the ball 402). In other words, the ball 402 generally displaces the full volume of the first section 410. As the ball 402 reaches the end of travel it will shut-off against a seat 414 and no more liquid can be expelled (FIG. 11). Thereafter, the dropper bottle 12 can be righted and the process repeated.

Figure 12:
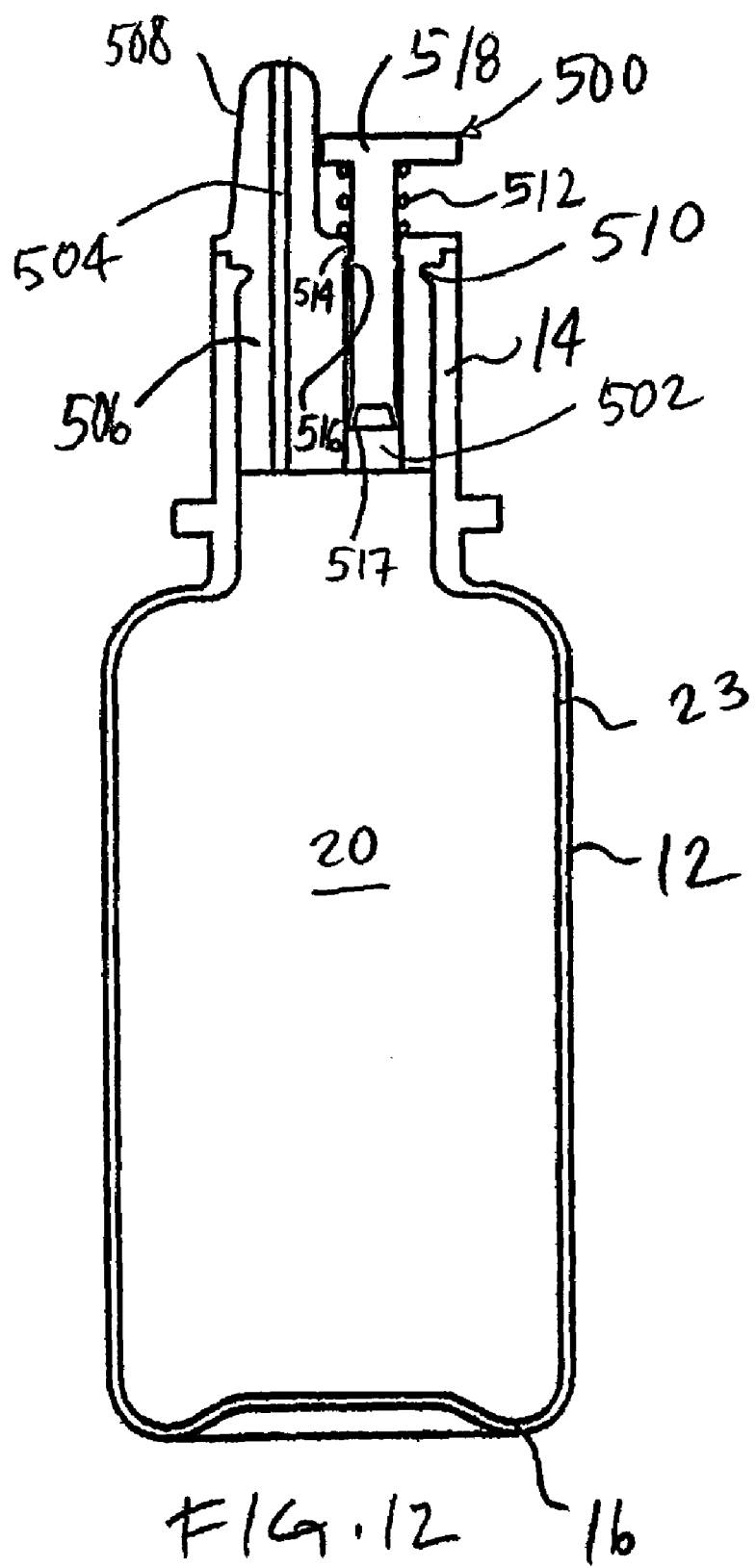
Figure 13:
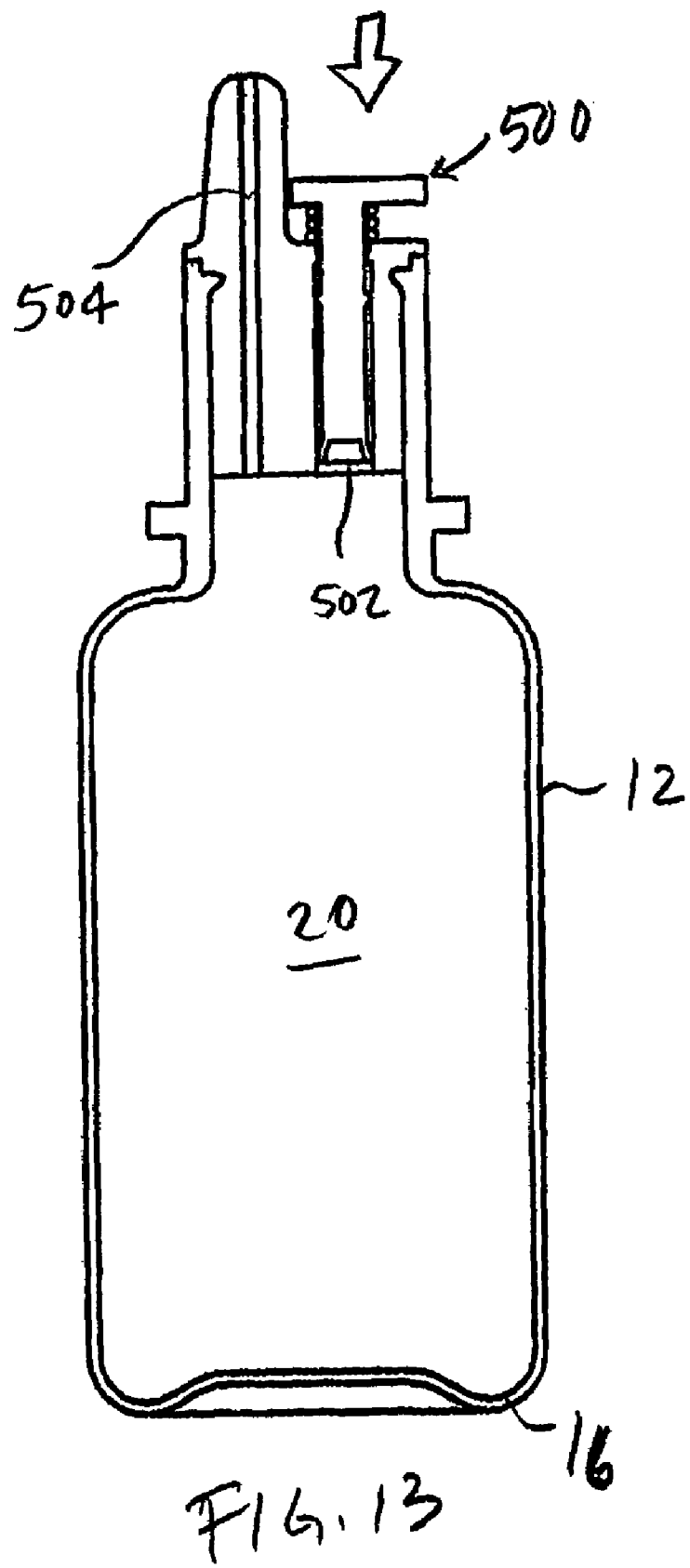

In a sixth aspect of the subject invention, an alternative to the above means of expelling a drop by deformation of a dropper bottle is provided by a piston 500 as shown in FIGS. 12-13. In this configuration, the piston 500 is displaceable from an initial position as shown in FIG. 12, and towards, possibly into, the reservoir 20 to an actuated position as shown in FIG. 13, so as to reduce the interior volume of the dropper bottle 12. Accordingly, a pressure rise is created in the bottle 12, and this rise in pressure causes a drop or dose to be expelled from the bottle 12 when the bottle 12 is inverted for use. As will be appreciated by those skilled in the art, the bottle 12 need not be deformable, since deformation is not required for dose administration.

The piston 500 extends through piston bore 502 which may be formed through plug 506 or the outer wall 23. To facilitate assembly, it is preferred that nozzle 508 be unitarily formed with the plug 506. The plug 506 may be fixed to the bottle 12 using any known method including an interference fit in the neck 14 of the bottle 12. A locking detent 510 may also be provided to enhance the fixation of the plug 506 to the bottle 12. Any known technique may be used to seal the piston bore 502 from leaking with the piston 500 being slidably disposed therein. For example, piston seal 517 may be provided as is known in the art to seal against the wall of the piston bore 502.

It is preferred that a spring 512 be provided to urge the piston 500 to an initial position, as shown in FIG. 12. As such, after use and release of the piston 500, the piston 500 may return to its initial position and be ready for subsequent dosing. Also, a shoulder 514 may be formed at the end of the piston bore 502 to coact with stop member 516 on the piston 500 to prevent excessive rearward movement of the piston 500 under force of the spring 512. A button 518 may further be provided on the piston 500 to provide a good surface against which a user may apply pressure in displacing the piston 500.

Figure 14:
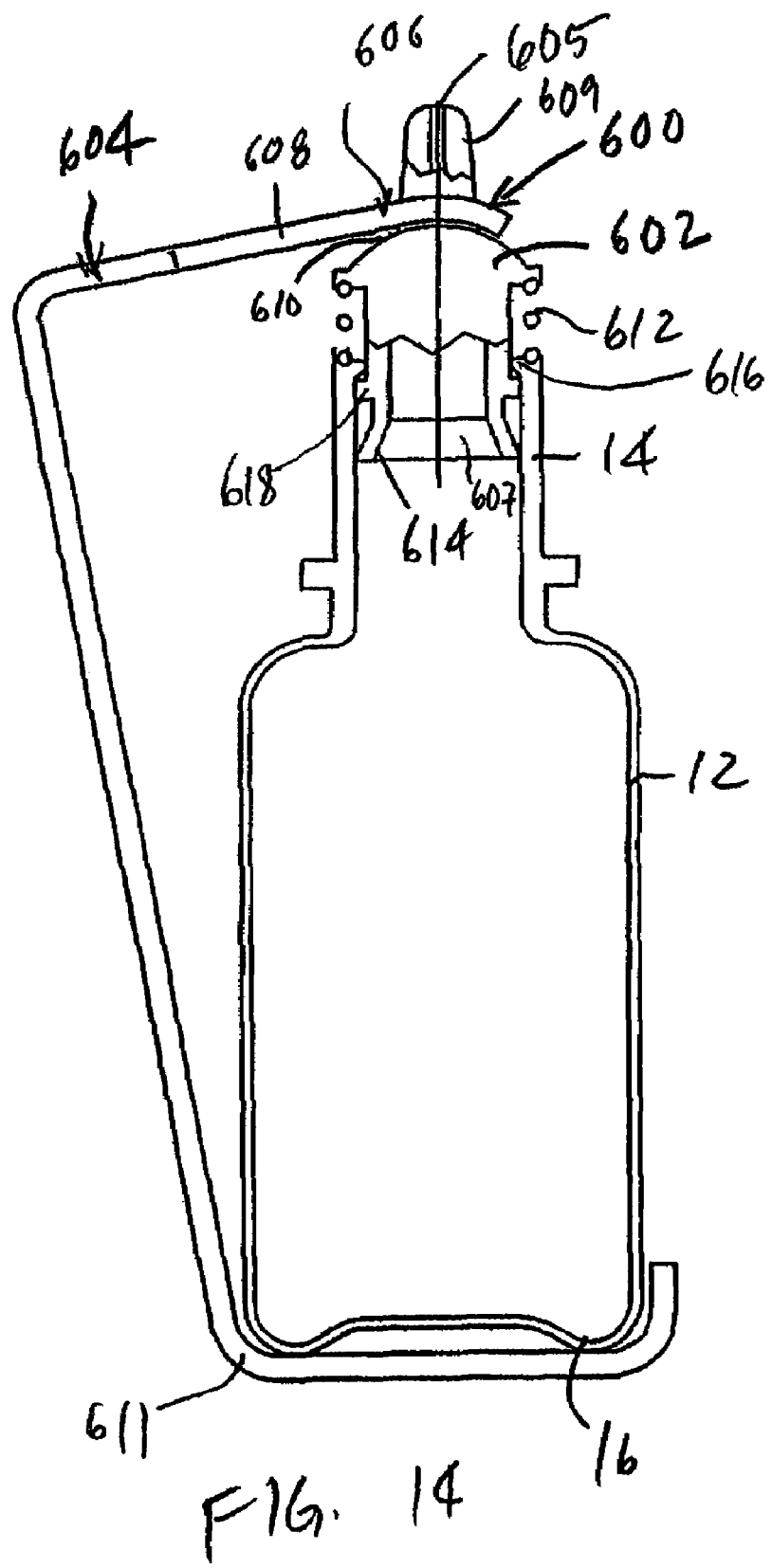
Figure 15:
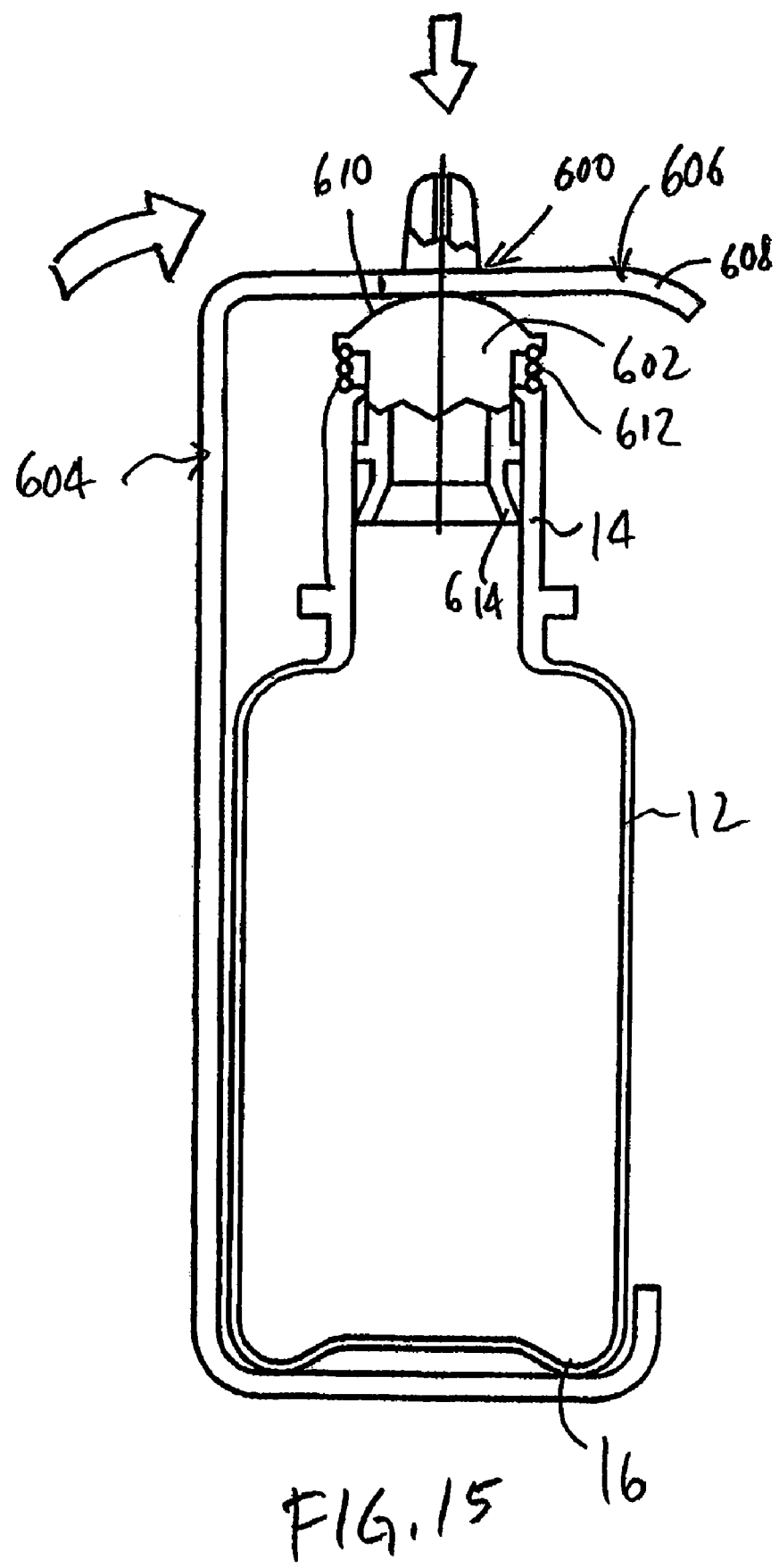
Figure 16:
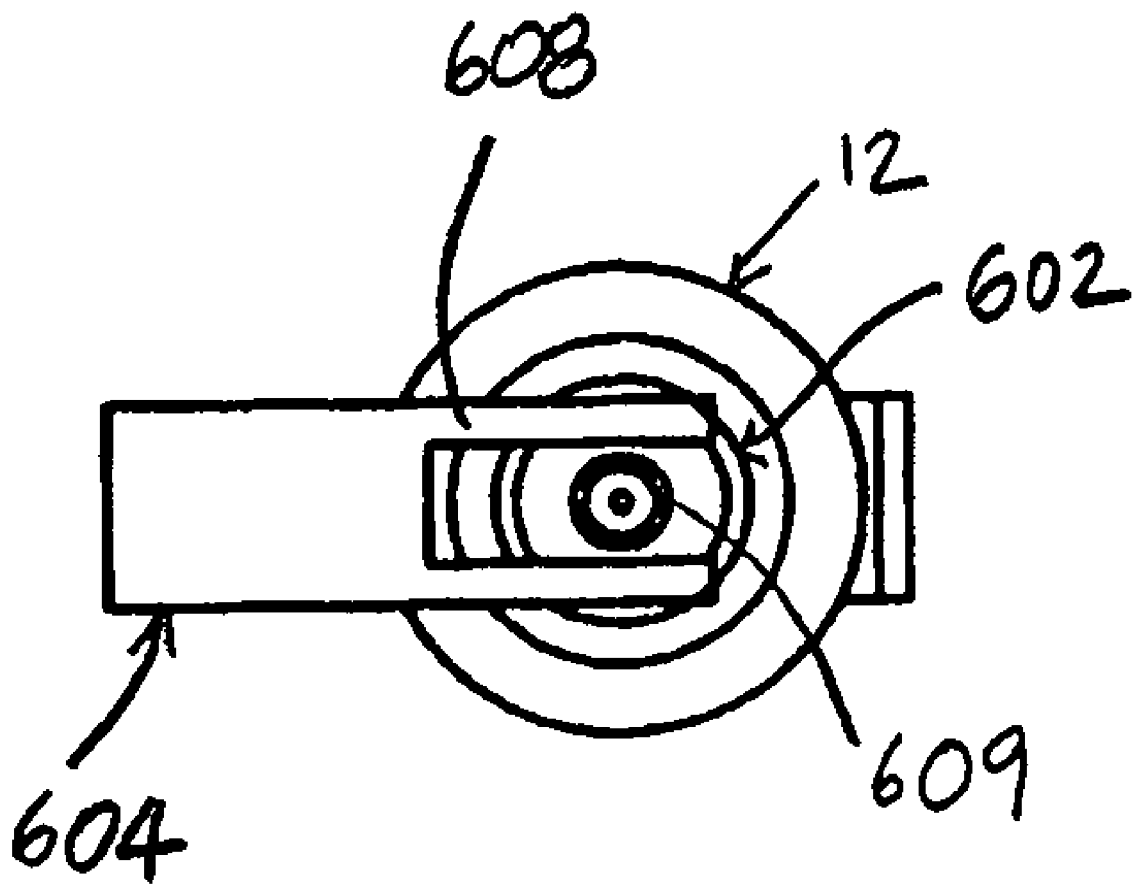

With reference to FIGS. 14-16, and as a variation of the sixth aspect of the subject invention, a device 600 is provided which includes a nozzle 602 that acts as a piston. More specifically, the nozzle 602 is displaceable within the bottle 12 to reduce the interior volume thereof. The nozzle 602 is disposed to translate within the neck 14. The nozzle 602 is formed with a discharge aperture 605 at one end in communication with an inlet opening 607 at the other end. Upon displacing the nozzle 602 downwardly to an actuated position as shown in FIG. 15, pressure within the interior volume of the dropper bottle 12 is increased resulting in fluid being displaced from the interior of the dropper bottle 12 through the nozzle 602 via the inlet opening 607 and out the discharge aperture 605. Piston seal 614 may be provided to cooperate with the neck 14 in defining a seal therewith. As with the previous design, the dropper bottle 12 need not be deformable.

The nozzle 602 is preferably biased by a spring 612 to an initial state as shown in FIG. 14. Shoulder 616 and stop member 618 can be provided to coact and prevent excessive rearward movement of the nozzle 602 under force of the spring 612.

Optionally, cradle 604 may be provided to facilitate actuation of the nozzle 602. The cradle 604 is preferably formed to resiliently snap about the dropper bottle 12 at the nozzle 602 and the bottle base 16, and is used to impart inward motion to the nozzle 602 (downward motion towards the base 16). To this end, a free end 606 of the cradle 604 is pressed transversely towards the bottle 12. As a result, a forked end 608 of the free end 606 translates across at least one rounded face 610 of the nozzle 602. As best shown in FIG. 16, the forked end 608 may straddle tip 609 of the nozzle 602 and provide stability of the cradle 604 relative to the dropper bottle 12. As the forked end 608 translates, the forked end 606 drives the nozzle 602 against the spring 612 (in the direction of the base 16) so that the nozzle 602 moves downwardly. This downward translation is achieved by the rotation of the forked end 608 about pivot 611. The rotation in effect shortens the radius of the forked end 608 in relation to the pivot 611, thus causing increased force to be applied against the rounded face 610. The interface of rounded surfaces between the forked end 608 and the rounded face 610 is desired to limit resistant frictional forces being defined therebetween. Upon release, the spring 612 urges the nozzle 602 upwardly. The memory of pivot 611 may also urge the cradle 604 to its initial state as shown in FIG. 14. It is preferred that the cradle 604 be formed of a resilient material, such as a resilient thermoplastic. To achieve a resilient holding force, the cradle 604 may be formed to overlap portions of the dropper bottle 12.

As is readily apparent, numerous modifications and changes may readily occur to those skilled in the art, and hence it is not desired to limit the invention to the exact construction operation as shown and described, and accordingly, all suitable modification equivalents may be resorted to falling within the scope of the invention as claimed.

What is claimed is:

1. A dropper bottle assembly comprising:
a dropper bottle including an interior volume; and,
a cradle mounted to said dropper bottle, said cradle including a movable lever arm, wherein movement of said lever arm causes a first portion of said lever arm to deform said dropper bottle in reducing said interior volume of said dropper bottle, whereby reduction of said interior volume causes fluid to be administered from said dropper bottle,
wherein said cradle includes a second portion defining a recess, and a second portion being formed on said lever arm to nest within said recess upon a predetermined extent of movement of said lever arm.

2. An assembly as in claim 1, wherein said second portion of said lever arm creates an audible signal upon nesting within said recess.

3. An assembly as in claim 1, said lever arm being hingedly connected to said second portion of said needle by a hinged connection.

4. An assembly as in claim 3, wherein said hinged connection urges said lever arm to a rest position where said dropper bottle is undeformed or substantially undeformed.

5. An assembly as in claim 3, wherein said lever arm includes a free end, said first portion of said lever arm being located intermediate said hinged connection and said free end.

6. An assembly as in claim 3, wherein said second portion of said cradle includes an aperture, said dropper bottle including a neck, said aperture being larger than said neck.

7. An assembly as in claim 6, wherein said first portion of said lever arm being formed to pressingly engage said dropper bottle to cause a portion of said neck to pressingly engage said second portion of said cradle located adjacent said aperture.

8. An assembly as in claim 1, wherein said dropper bottle includes an indented bottom surface, said second portion of said cradle being formed to seat within and press against said indented bottom.

\* \* \* \* \*

UNITED STATES PATENT AND TRADEMARK OFFICE
CERTIFICATE OF CORRECTION

PATENT NO.      : 7,635,070 B2
APPLICATION NO. : 10/523516
DATED           : December 22, 2009
INVENTOR(S)     : Cohen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1089 days.

Signed and Sealed this

Twenty-first Day of December, 2010

David J. Kappos
*Director of the United States Patent and Trademark Office*